United States Patent
Leal et al.

(10) Patent No.: US 11,427,518 B2
(45) Date of Patent: Aug. 30, 2022

(54) METHOD OF PRODUCING A FUEL ADDITIVE

(71) Applicants: SABIC Global Technologies B.V., Bergen op Zoom (NL); Saudi Arabian Oil Company, Dhahran (SA)

(72) Inventors: Guillermo Leal, Riyadh (SA); Naif Mohammed Al-Naddah Al-Otaibi, Riyadh (SA); Mohammed Bismillah Ansari, Riyadh (SA); Kareemuddin Mahaboob Shaik, Dhahran (SA); Hiren Shethna, Dhahran (SA); Zhonglin Zhang, Dhahran (SA)

(73) Assignees: SAUDI ARABIAN OIL COMPANY, Dhahran (SA); SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/981,183

(22) PCT Filed: Mar. 18, 2019

(86) PCT No.: PCT/IB2019/052177
§ 371 (c)(1),
(2) Date: Sep. 15, 2020

(87) PCT Pub. No.: WO2019/180584
PCT Pub. Date: Sep. 26, 2019

(65) Prior Publication Data
US 2021/0002185 A1 Jan. 7, 2021

Related U.S. Application Data

(60) Provisional application No. 62/644,626, filed on Mar. 19, 2018.

(51) Int. Cl.
*C07C 4/04* (2006.01)
*C07C 5/03* (2006.01)
(Continued)

(52) U.S. Cl.
CPC .............. *C07C 4/04* (2013.01); *C07C 5/03* (2013.01); *C07C 5/05* (2013.01); *C07C 29/04* (2013.01);
(Continued)

(58) Field of Classification Search
CPC .......... C10L 10/10; C10L 1/14; C10L 1/1608; C10L 1/1616; C10L 1/1824; C07C 29/04;
(Continued)

(56) References Cited

U.S. PATENT DOCUMENTS 3,061,654 A 10/1962 Gensheimer et al.
3,797,690 A 3/1974 Taylor et al.
(Continued)

FOREIGN PATENT DOCUMENTS

CA 2018524 A1 12/1990
CN 1044804 C 8/1999
(Continued)

OTHER PUBLICATIONS

Brockwell et al.; "Synthesize ethers"; Hydrocarbon Processing, vol. 70, No. 9; 1991; pp. 133-141.
(Continued)

*Primary Examiner* — Latosha Hines
(74) *Attorney, Agent, or Firm* — Cantor Colburn LLP

(57) ABSTRACT

A method of producing a fuel additive includes producing a first product stream comprising butadiene by passing a feed stream comprising C4 hydrocarbons through a steam cracker; transforming greater than or equal to 90 weight % of the butadiene in the first product stream into a second product stream by passing the first product stream through a
(Continued)

first hydrogenation unit, wherein the second product stream comprises 1-butene, 2-butene, n-butane, isobutylene, isobutane, or a combination thereof; and converting the second product stream into the fuel additive by passing the second product stream through a fuel additive synthesis unit with an acid catalyst.

20 Claims, 1 Drawing Sheet

(51) Int. Cl.
    *C07C 5/05*         (2006.01)
    *C07C 29/04*       (2006.01)
    *C10L 1/16*         (2006.01)
    *C10L 1/182*       (2006.01)
    *C10L 10/10*       (2006.01)

(52) U.S. Cl.
    CPC ........... *C10L 1/1608* (2013.01); *C10L 1/1824* (2013.01); *C10L 10/10* (2013.01); *C07C 2521/04* (2013.01)

(58) Field of Classification Search
    CPC ........... C07C 41/06; C07C 5/05; C07C 11/08; C07C 31/12; C07C 43/046; C07C 2521/04; C07C 2523/44; C07C 2523/46; C07C 2523/72; C07C 2523/75; C07C 2523/755; C07C 4/04; C07C 5/03
    See application file for complete search history.

(56) References Cited

U.S. PATENT DOCUMENTS

| | | | |
|---|---|---|---|
| 3,849,082 A | 11/1974 | Kozlowski et al. | |
| 3,912,463 A | 10/1975 | Kozlowski et al. | |
| 4,324,936 A | 4/1982 | Mikulicz | |
| 4,334,890 A | 6/1982 | Kochar et al. | |
| 4,336,046 A | 6/1982 | Schorre et al. | |
| 4,356,339 A | 10/1982 | Imaizumi et al. | |
| 4,408,085 A | 10/1983 | Gottlieb et al. | |
| 4,423,251 A | 12/1983 | Pujado et al. | |
| 4,436,946 A | 3/1984 | Smitny | |
| 4,455,445 A | 6/1984 | Neuzil et al. | |
| 4,499,313 A | 2/1985 | Okumura et al. | |
| 4,540,831 A | 9/1985 | Briggs | |
| 4,773,968 A | 9/1988 | O'Connell et al. | |
| 4,783,555 A | 11/1988 | Atkins | |
| 4,797,133 A * | 1/1989 | Pujado ................... C10L 1/023 44/449 | |
| 4,927,977 A | 5/1990 | Child et al. | |
| 5,227,553 A * | 7/1993 | Polanek ................... C07C 5/05 585/841 | |
| 5,254,748 A | 10/1993 | Hensley et al. | |
| 5,382,707 A | 1/1995 | Rubin et al. | |
| 5,523,502 A | 6/1996 | Rubin | |
| 5,563,299 A | 10/1996 | Paludetto et al. | |
| 5,628,880 A | 5/1997 | Hearn et al. | |
| 5,672,795 A | 9/1997 | Vora et al. | |
| 5,877,365 A | 3/1999 | Chodorge et al. | |
| 5,898,091 A | 4/1999 | Chodorge et al. | |
| 5,955,640 A | 9/1999 | Paludetto et al. | |
| 7,227,047 B2 | 6/2007 | Risch et al. | |
| 7,473,812 B2 | 1/2009 | Peters et al. | |
| 7,485,761 B2 | 2/2009 | Schindler et al. | |
| 8,124,572 B2 | 2/2012 | Miller | |
| 8,395,007 B2 | 3/2013 | Wright et al. | |
| 8,999,013 B2 | 4/2015 | Xu et al. | |
| 9,187,388 B2 | 11/2015 | Arjah et al. | |
| 9,611,192 B2 | 4/2017 | Digiulio | |
| 10,774,020 B2 | 9/2020 | Di Girolamo et al. | |
| 2002/0169346 A1 | 11/2002 | Commereuc et al. | |
| 2003/0158429 A1 | 8/2003 | Albiez et al. | |
| 2004/0171891 A1 | 9/2004 | Scholz et al. | |
| 2005/0043575 A1* | 2/2005 | Risch .................... C10G 45/02 585/324 |
| 2005/0288534 A1 | 12/2005 | Fernandez et al. | |
| 2007/0149839 A1 | 6/2007 | Rix et al. | |
| 2007/0265483 A1 | 11/2007 | Himelfarb | |
| 2008/0146858 A1 | 6/2008 | Elomari et al. | |
| 2008/0312481 A1 | 12/2008 | Leyshon | |
| 2009/0193710 A1* | 8/2009 | Xiong ................... C10L 1/1852 44/449 |
| 2011/0040133 A1 | 2/2011 | Vermeiren et al. | |
| 2011/0230632 A1* | 9/2011 | Abhari ................... C10G 9/36 526/348 |
| 2012/0117862 A1 | 5/2012 | Xu | |
| 2012/0283492 A1 | 11/2012 | Dalemat et al. | |
| 2013/0072732 A1 | 3/2013 | Breuil et al. | |
| 2013/0104449 A1 | 5/2013 | Xu et al. | |
| 2013/0172627 A1 | 7/2013 | Chewter et al. | |
| 2013/0331620 A1 | 12/2013 | Abhari | |
| 2014/0039226 A1 | 2/2014 | Xu et al. | |
| 2014/0142350 A1 | 5/2014 | Weiner et al. | |
| 2015/0225320 A1 | 8/2015 | Shaik et al. | |
| 2015/0322181 A1 | 11/2015 | Kim et al. | |
| 2016/0326079 A1 | 11/2016 | Lee et al. | |
| 2017/0073289 A1* | 3/2017 | Leal ....................... C07C 7/167 |
| 2017/0198231 A1 | 7/2017 | Xu et al. | |
| 2017/0253540 A1 | 9/2017 | Hofel et al. | |
| 2020/0157450 A1 | 5/2020 | Leal et al. | |
| 2021/0024837 A1 | 1/2021 | Leal et al. | |
| 2021/0024843 A1 | 1/2021 | Leal et al. | |
| 2021/0155862 A1 | 5/2021 | Leal et al. | |
| 2021/0171848 A1 | 6/2021 | Leal et al. | |
| 2021/0214290 A1 | 7/2021 | Ansari et al. | |
| 2021/0246088 A1 | 8/2021 | Leal et al. | |

FOREIGN PATENT DOCUMENTS

| | | |
|---|---|---|
| CN | 1506344 A | 6/2004 |
| CN | 1736589 A | 2/2006 |
| CN | 101279879 A | 10/2008 |
| CN | 102070391 A | 5/2011 |
| CN | 105585411 A | 5/2016 |
| CN | 106608791 A | 5/2017 |
| CN | 102372573 A | 3/2021 |
| EP | 0063813 B1 | 11/1982 |
| EP | 0102840 B1 | 3/1984 |
| EP | 0253679 | 1/1988 |
| EP | 0605822 A1 | 7/1994 |
| GB | 1374368 | 11/1974 |
| JP | S5920232 A | 2/1984 |
| JP | 2010111596 A | 5/2010 |
| RU | 2470905 C1 | 12/2012 |
| WO | 9011268 | 10/1990 |
| WO | 9732838 A1 | 9/1997 |
| WO | 0043336 A1 | 7/2000 |
| WO | 0146095 A1 | 6/2001 |
| WO | 2006113191 A2 | 10/2006 |
| WO | 2007024733 A2 | 3/2007 |
| WO | 2012095744 A2 | 7/2012 |
| WO | 2014153570 A2 | 9/2014 |
| WO | 2014160825 A1 | 10/2014 |
| WO | 2015089005 A1 | 6/2015 |
| WO | 2015123026 A1 | 8/2015 |
| WO | 2019207477 A1 | 10/2019 |

OTHER PUBLICATIONS

International Search Report for International Application No. PCT/IB2019/052178; International Filing Date Mar. 18, 2019; dated Jun. 26, 2019; 6 pages.

International Search Report for International Application No. PCT/IB2019/053697; International Filing Date May 6, 2019; dated Aug. 28, 2019; 11 pages.

International Search Report for International Application No. PCT/IB2019/057784; International Filing Date Sep. 16, 2019; dated Jan. 7, 2020; 5 pages.

(56) References Cited

OTHER PUBLICATIONS

International Search Report for International Application No. PCT/US2019/026985; International Filing Date Apr. 11, 2019; dated May 27, 2019; 6 pages.
International Search Report for International Application No. PCT/US2019/028092; International Filing Date Apr. 18, 2019; dated Jun. 26, 2019; 6 pages.
International Search Report for International Application No. PCT/US2019/028099; International Filing Date Apr. 18, 2019; dated Jun. 26, 2019; 6 pages.
International Search Report; International Application No. PCT/IB2018/055647; International Filing Date: Jul. 27, 2018; dated Oct. 30, 2018; 6 pages.
Izquierdo et al.; "Equilibrium Constants for Methyl tert-Butyl Ether Liquid-Phas Synthesis"; J. Chem. Eng. Data, vol. 37; 1992; pp. 339-343.
Kalamaras et al.; "SuperButol—A novel high-octane gasoline blending component"; Fuel, vol. 195; 2017; pp. 165-173.
Streich et al.; "Secure the Best Benefits from C4 Hydrocarbon Processing—Part 1: Separation Sequences"; Hydrocarbon Processing: Process Engineering and Optimization; 2016; 6 pages.
Written Opinion for International Application No. PCT/IB2019/052178; International Filing Date Mar. 18, 2019 dated Jun. 26, 2019; 9 pages.
Written Opinion for International Application No. PCT/IB2019/053697; International Filing Date May 6, 2019; dated Aug. 28, 2019; 9 pages.
Written Opinion for International Application No. PCT/IB2019/057784; International Filing Date Sep. 16, 2019; dated Jan. 7, 2020; 7 pages.
Written Opinion for International Application No. PCT/US2019/026985; International Filing Date Apr. 11, 2019; dated May 27, 2019; 7 pages.
Written Opinion for International Application No. PCT/US2019/028092; International Filing Date Apr. 18, 2019; dated Jun. 26, 2019; 9 pages.
Written Opinion for International Application No. PCT/US2019/028099; International Filing Date Apr. 18, 2019; dated Jun. 26, 2019; 13 pages.
Written Opinion; International Application No. PCT/IB2018/055647; International Filing Date: Jul. 27, 2018; dated Oct. 30, 2018; 11 pages.
Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.
International Search Report for International Application No. PCT/IB2019/052177; International Filing Date Mar. 18, 2019; dated Jun. 26, 2019; 3 pages.
Written Opinion for International Application No. PCT/IB2019/052177; International Filing Date Mar. 18, 2019; dated Jun. 26, 2019; 9 pages.
International Search Report for International Application No. PCT/IB2019/059984; International Filing Date Nov. 20, 2019; dated Feb. 21, 2020; 5 pages.
Written Opinion for International Application No. PCT/IB2019/059984; International Filing Date Nov. 20, 2019; dated Feb. 21, 2020; 8 pages.
Bodas et al.; U.S. Appl. No. 17/292,261; entitled "Process and System for Producing Ethylene and at Least One of Butanol and an Alkyl Tert-Butyl Ether"; filed May 7, 2021.
International Search Report for International Application No. PCT/IB2020/051908; International Filing Date Mar. 5, 2020; dated May 29, 2020; 6 pages.
Leal et al. U.S. Appl. No. 17/436,753, entitled "Method of Producing a Fuel Additive", filed Sep. 7, 2021.
Written Opinion for International Application No. PCT/IB2020/051908; International Filing Date Mar. 5, 2020; dated May 29, 2020; 9 pages.
Fuel Additives Selection Guide: Types, Features, Applications, Engineering 360, 4 pages, obtained May 11, 2022, http://www.globalspec.com/learnmore/materials_chemicals_adhesives/industrial_oils_fluids/fuel_oil_fluid_additives (Year: 2022).

\* cited by examiner

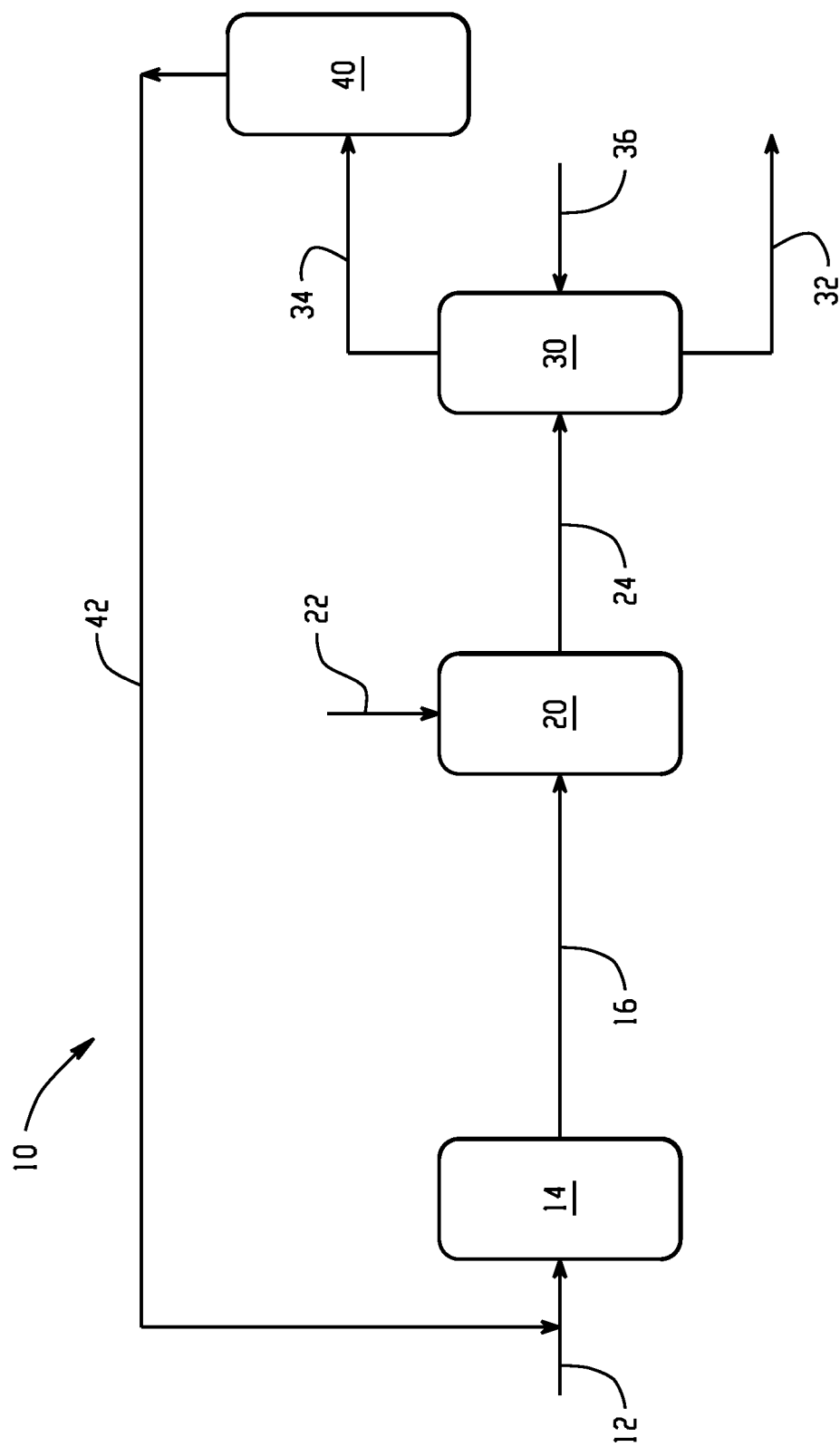

METHOD OF PRODUCING A FUEL ADDITIVE

CROSS REFERENCE TO RELATED APPLICATIONS

This application is a National Stage application of PCT/IB2019/052177, filed Mar. 18, 2019, which is incorporated herein by reference in its entirety, and which claims the benefit of U.S. Provisional Application No. 62/644,626, filed Mar. 19, 2018.

BACKGROUND

Commercial gasoline, which is fuel for internal combustion engines, is a refined petroleum product that is typically a mixture of hydrocarbons (base gasoline), additives, and blending agents. Additives and blending agents are added to the base gasoline to enhance the performance and the stability of gasoline, for example octane boosters.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking (FCC) is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (C1-C35). The effluent can then be separated into individual olefins (for example, ethylene, propylene and C4's) and pyrolysis gasoline. Recycle streams of crude hydrocarbons are often formed as by-products during these cracking processes.

The presence of isobutylene, butadiene, 1-butene, 2-butene, and other components within the crude hydrocarbon streams can allow for the formation of valuable alcohols and fuel additives. Such alcohols can include methanol, which is commonly used as a gasoline octane booster. However, the conversion of crude hydrocarbon streams to fuel additive products can often be inefficient and costly. Furthermore, the final product specifications for such alcohols (e.g., methanol) can be undesirable and can fail to meet market quality requirements. For example, alcohol products can have high levels of impurities, high Reid vapor pressures (RVP) of greater than 10 kilopascals (greater than 2.0 pounds per square inch (psi), and low octane numbers (e.g., Research Octane Number (RON)) less than 82, all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with low impurities and high performance specifications.

SUMMARY

Disclosed, in various embodiments, are methods of producing fuel additives.

A method of producing a fuel additive includes: producing a first product stream comprising butadiene by passing a feed stream comprising C4 hydrocarbons through a steam cracker; transforming greater than or equal to 90 weight % of the butadiene in the first product stream into a second product stream by passing the first product stream through a first hydrogenation unit, wherein the second product stream comprises 1-butene, 2-butene, n-butane, isobutylene, isobutane, or a combination thereof; and converting the second product stream into the fuel additive by passing the second product stream through a fuel additive synthesis unit with an acid catalyst.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

FIG. 1 is a schematic diagram representing a unit sequence for producing a fuel additive.

The above described and other features are exemplified by the following detailed description and claims.

DETAILED DESCRIPTION

Disclosed herein is an efficient method of producing a fuel additive that can make use of crude hydrocarbon streams and produce final products with low impurities and high performance specifications. For example, the method disclosed herein can provide a unique sequence of unit operations that converts crude hydrocarbons into valuable fuel additives, such as alcohol fuel additives. This unique sequence can significantly improve the efficiency of the method, thereby reducing total capital costs. The fuel additive can have levels of trimethylpentane of 0.01 weight % to 50 weight %, based on the total weight of the fuel additive, high octane numbers (e.g., greater than or equal to 85 RON, or greater than or equal to 87 RON), and low Reid vapor pressures of greater than or equal to 55 Kilopascals. Any one or all of these properties can correlate with high performance and high market value.

The method of producing a fuel additive disclosed herein can utilize a first hydrogenation unit integrated with a steam cracker and a fuel additive synthesis unit to reduce capital expenditure and increase fuel additive production by transforming greater than or equal to 90 weight % of butadiene in a first product stream produced by the steam cracker into 1-butene and 2-butene (collectively "butene") in a second product stream. In order to order to achieve an increase in the production of 1-butene and 2-butene from the butadiene present in the first product stream, the first hydrogenation unit can be a selective hydrogenation unit. For example, less than or equal to 5 weight %, for example, less than or equal to 5 weight %, of butadiene can be present in the second product stream, based on the total weight of the second product stream. The second product stream is converted into the fuel additive by passing the second product stream through the fuel additive synthesis unit with an acid catalyst.

A method of producing a fuel additive can include producing a first product stream comprising butadiene by passing a feed stream comprising C4 hydrocarbons through a steam cracker, transforming greater than or equal to 90 weight % of the butadiene in the first product stream into a second product stream by passing the first product stream through a first hydrogenation unit, and converting the second product stream into a fuel additive by passing the second product stream through a fuel additive synthesis unit with an acid catalyst.

As used herein "C4 hydrocarbons" refers to hydrocarbons including four or more carbon atoms.

The step of passing a feed stream through a steam cracker can include passing a feed stream comprising a portion of an effluent from a fluid catalytic cracking process through a steam cracker. Additionally, a source of the feed stream can include a product of an olefin cracking process and/or an olefin production process. The feed stream can comprise hydrocarbons, for example, C4 hydrocarbons. Additional hydrocarbons, for example, C2 and C3 hydrocarbons, can also be fed to the olefin production process. The feed stream can then be withdrawn from the olefin production process as a crude C4 hydrocarbon stream. In an embodiment, the feed stream includes methyl acetylene, propylene, 1,3-butadiene, 1,2-butadiene, isobutylene, cis-2-butene, trans-2-butene, 1-butene, propene, isobutane, n-butane, or a combination thereof.

The steam cracker can produce a first product stream comprising butadiene. The first product stream can comprise butadiene in an amount less than or equal to 75 weight %, for example, less than or equal to 50 weight %, for example, less than or equal to 40 weight %, based on the total weight of the first product stream. The first product stream also can include 1-butene, 2-butene, isobutylene, n-butane, isobutane, or a combination thereof.

As used herein, the term "steam cracker" relates to a unit for use in a petrochemical process in which saturated hydrocarbons are broken down into smaller, often unsaturated, hydrocarbons such as ethylene and propylene. In steam cracking, gaseous hydrocarbon feeds are diluted with steam and briefly heated to a reaction temperature in a furnace without the presence of oxygen.

Steam can be fed through the steam cracker via a steam stream.

A temperature within the steam cracker can be 700° C. to 900° C., for example, 725° C. to 875° C. A pressure within the steam cracker can be 50 kilopascals (kPa) to 500 kPa, for example, 100 kilopascals to 350 kilopascals. A coil outlet temperature (COT) can be 800 to 850° C., a coil outlet pressure (COP) can be 150 kPa to 250 kPa (1.5 to 2.5 bar), a stream ratio (SR) of 0.2 to 0.4 kilograms (kg), and an inlet temperature (Tin) of 500 to 700° C.

The method for producing a fuel additive can also include transforming greater than or equal to 90 weight %, for example, greater than or equal to 95 weight %, for example, greater than or equal to 96 weight %, of the butadiene in the first product stream into the second product stream.

Desirably, the first product stream can be passed through a first hydrogenation unit comprising a selective hydrogenation unit. For example, the selective hydrogenation unit can be a selective butadiene hydrogenation unit. The first hydrogenation unit can convert butadiene present in the first product stream to 1-butene and 2-butene. The yield for converting butadiene to 2-butene can be greater than or equal to 30% and the yield for converting butadiene to 1-butene can be greater than or equal to 65%. It should be understood, however, the selectivities for 1-butene or 2-butene can be shifted depending on the requirements of downstream units.

The first hydrogenation unit can comprise multiple reactors in series, for example, the first hydrogenation unit can comprise three reactors. The first two reactors can convert butadiene present in the first product stream to 1-butene and 2-butene. The first two reactors can comprise a hydrogenation catalyst. For example, the hydrogenation catalyst can include platinum, rhodium, palladium, ruthenium, cobalt, nickel, copper, or a combination thereof. In an embodiment, the hydrogenation catalyst includes palladium with an aluminum (e.g., alumina) support. The hydrogenation catalyst can be the same for the first two reactors.

Hydrogen can be injected into the first product stream prior to passing through the first reactor.

Hydrogenation reaction of di-olefins to mono-olefins can be achieved in a third reactor. Carbon monoxide can be injected into the third reactor to attenuate the hydrogenation catalyst and minimize the isomerization reaction from 1-butene to 2-butene. The carbon monoxide injection rate can be 2 parts per million (by weight) of the feed rate to the third reactor. If too much 1-butene is converted to 2-butene, the second product stream can be withdrawn from the first reactor.

Exemplary temperatures, pressures, and hydrogenation catalysts within the hydrogenation reactors, along with exemplary amounts of butadiene (BD) present in the reactor effluent are summarized in Table 1. Temperature was measured in degrees Celsius (° C.), pressure in kilopascals (kPa) and pounds per square inch gauge (psig), along with butadiene (BD) content at the exit in each reactor stage.

TABLE 1

| Reactor | Temperature ° C. | Pressure kPa (psig) | Catalyst | BD of Reactor Effluent (weight %) |
| --- | --- | --- | --- | --- |
| 1st Reactor | 40 to 70 | 965 to 2,758 (140-400) | Noble metal/Alumina | 7% |
| 2nd Reactor | 50 to 60 | 965 to 2758 (140-400) | Noble metal/Alumina | 1% |
| 3rd Reactor | 60 to 80 | 1,724-1,862 (250-270) | Noble metal/Alumina | <0.01% |

The method of producing a fuel additive can further include converting the second product stream into a fuel additive by passing the second product stream into a fuel additive synthesis unit with an acid catalyst. The second product stream can include 1-butene, 2-butene, n-butane, isobutylene, isobutane, or a combination thereof. The second product stream passed through the fuel additive synthesis unit can comprise butadiene in an amount of less than or equal to 5 weight %, for example, less than or equal to 3 weight %, for example, less than or equal to 1 weight %, based on the total weight of the second product stream. Desirably, the second product stream includes a low amount of isobutylene. For instance, isobutylene can be present in the second product stream in an amount of less than or equal to 10 weight %, for example, less than or equal to 5%, based on the total weight of the second product stream. Butene (i.e., 1-butene and 2-butene) can be present in the second product stream in an amount of greater than or equal to 0.01 weight %, for example, 0.25 weight % to 50 weight %, based on the total weight of the second product stream. The weight ratio of 2-butene to 1-butene in the second product stream can be 0.1 to 0.7, for example, 0.2 to 0.6, for example, 0.3 to 0.5.

The method of producing a fuel additive can include converting butene present in the second product stream to butanol. For example, greater than or equal to 75 weight % of the butene present in the second product stream, based on the total weight of the second product stream, can be converted to butanol within the fuel additive synthesis unit.

The acid catalyst for converting the second product stream into a fuel additive can include phosphoric acid, sulfonic acid, sulfuric acid, nitric acid, hypophosphorous acid, metal oxide, zeolite, or a combination thereof. For instance, the acid catalyst can include a sulfonic acid resin, sulfonated polystyrene, hypophosphorous acid, supported niobium oxide, zeolite supported acid catalyst, or a combination thereof.

Desirably, the second product stream can be converted into a fuel additive at a temperature of 25° C. to 300° C., preferably 30° C. to 250° C., more preferably 140° C. to 200° C. The second product stream can be converted into a fuel additive at a pressure of 0.25 MegaPascal to 20 MegaPascal, preferably 0.5 MegaPascals to 10 MegaPascals, more preferably 5 MegaPascals to 10 MegaPascal.

Desirably, the method of producing a fuel additive further includes passing a water stream through the fuel additive synthesis unit. A molar ratio of water to butene fed to the fuel additive synthesis unit can be 0.5 to 25, for example, 1 to 20.

The method of producing a fuel additive can further include withdrawing a by-product stream from the fuel additive synthesis unit and passing the by-product stream through a second hydrogenation unit. The by-product stream can include 1-butene, 2-butene, isobutane, n-butane, or a combination thereof.

Desirably, the method for producing a fuel additive further includes withdrawing a recycle stream from the second hydrogenation unit. The recycle stream can include n-butane, isobutane, or a combination thereof, and recycling the recycle stream back to the feed stream.

The method for producing a fuel additive can further include passing the recycle stream through the steam cracker to produce propylene, ethylene, or a combination thereof.

The first hydrogenation unit and/or the second hydrogenation unit can include an oscillating baffle reactor, a fixed bed reactor, a fluidized bed reactor, a membrane integrated reactor, or a combination thereof.

The fuel additive synthesis unit comprises an oscillating baffle reactor, a fixed bed reactor, multitubular reactor, a membrane integrated reactor, a reactive distillation unit, or a combination thereof.

The method of producing a fuel additive can further include withdrawing a fuel additive from the fuel additive synthesis unit. The fuel additive can include 2-butanol, tert-butyl alcohol, C4 dimer, or a combination thereof. The C4-dimer can include di-isobutylene, 2,2,4 trimethylpentane, 2,3,3 trimethylpentane, or a combination thereof.

In an embodiment, the fuel additive includes trimethylpentane in an amount greater than or equal to 0.01 weight %, for example, greater than or equal to 0.02 weight %, for example, greater than or equal to 0.1 weight %, based on the total weight of the fuel additive.

The fuel additive can also comprise less than or equal to 1 weight % impurities such as diene, based on the total weight of the fuel additive. For example, the fuel additive can comprise less than or equal to 0.1 weight % of butylene dimers, based on the total weight of the fuel additive.

A Research Octane Number (RON) of the fuel additive can be greater than or equal to 85, for example, greater than or equal to 86. The Research Octane Number is determined by running the fuel additive in a test engine at a speed of 600 revolutions per minute with a variable compression ratio under controlled conditions, and comparing the results with those for mixtures of iso-octane and n-heptane. Thus, the Research Octane Number gages the performance the fuel additive. The higher the Research Octane Number, the more compression the fuel additive is able to withstand before igniting. Fuel additives with higher Research Octane Number ratings are generally used in high performance gasoline engines that need higher compression ratios. Fuels with lower Research Octane Numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

Fuel additives with a higher RON can require higher amounts of energy needed to initiate combustion. Fuels with higher RON are less prone to auto-ignition and can withstand a greater rise in temperature during the compression stroke of an internal combustion engine without auto-igniting.

A Motor Octane Number of the fuel additive can be 8 to 12 octanes lower than the Research Octane Number. The Motor Octane Number can be greater than or equal to 82, for example, greater than or equal to 85, for example, greater than or equal to 87, for example, greater than or equal to 90. Motor Octane Number is determined by testing a similar test engine to that used in determining the Research Octane Number but at a speed of 900 revolutions per minute with a preheated fuel mixture, higher engine speed, and variable ignition timing.

A Reid vapor pressure of the fuel additive can be less than or equal to 55 kilopascals, for example, 8 kilopascals to 53 kilopascals, for example, 10 kilopascals to 51 kilopascals. Reid vapor pressure is used to measure the volatility of gasoline defined as the absolute vapor pressure exerted by a liquid at 37.8° C. as determined by ASTM D-323. This measures the vapor pressure of gasoline volatile crude oil, and other volatile petroleum products, except for liquefied petroleum gases. Reid vapor pressure is measured in kilopascals and represents a relative pressure to atmospheric pressure since ASTM D-323 measures the gage pressure of the sample in a non-evacuated chamber. High levels of vaporization are desired for winter starting and operation and lower levels are desirable in avoiding vapor lock during summer heat. Fuel cannot be pumped when vapor is present in the fuel line and winter starting will be difficult when liquid gasoline in the combustion chambers has not vaporized. This means that the Reid vapor pressure is changed accordingly by oil producers seasonally to maintain gasoline engine reliability. The Reid vapor pressure can vary during winter and summer conditions such that the pressure can be at the higher end of the values during the winter and at the lower end of the values during the summer.

A more complete understanding of the components, processes, and apparatuses disclosed herein can be obtained by reference to the accompanying drawings. These FIGURES (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to FIG. 1, this simplified schematic diagram represents a unit sequence 10 used in a method of producing a fuel additive. The unit sequence 10 can include passing a feed stream 12 comprising C4 hydrocarbons through a steam cracker 14.

A first product stream 16 comprising butadiene is produced from the steam cracker 14. The first product stream 16 can then be passed through a first hydrogenation unit 20. Hydrogen 22 can be fed to the first hydrogenation unit 20. The first hydrogenation unit 20 can be a selective butadiene hydrogenation unit and can comprise multiple reactors in series. The first hydrogenation unit 20 can transform the butadiene in the first product stream 16 into a second product stream 24 comprising 1-butene and 2-butene as previously described in detail herein.

The second product stream 24 can then be withdrawn from the first hydrogenation unit 20 and passed through a fuel additive synthesis unit 30 to produce a fuel additive 32, such as an alcohol fuel additive. The fuel additive 32 can be withdrawn from the fuel additive synthesis unit 30. Water 36 can be fed to the fuel additive synthesis unit 30.

A by-product stream 34 can be withdrawn from the fuel additive synthesis unit 30 and passed through a second hydrogenation unit 40, e.g., a C4 hydrogenation unit. A recycle stream 42 can be produced in the second hydrogenation unit 40. The second hydrogenation unit 40 can convert the 1-butene and 2-butene present in the by-product 34 to n-butane and isobutane in the recycle stream 42. The resulting recycle stream 42 can then recycled back to the feed stream 12.

The methods disclosed herein include(s) at least the following aspects:

Aspect 1: A method of producing a fuel additive, comprising: producing a first product stream comprising butadiene by passing a feed stream comprising C4 hydrocarbons through a steam cracker; transforming greater than or equal to 90 weight % of the butadiene in the first product stream into a second product stream by passing the first product stream through a first hydrogenation unit, wherein the second product stream comprises 1-butene, 2-butene, n-butane, isobutylene, isobutane, or a combination thereof; and converting the second product stream into the fuel additive by passing the second product stream through a fuel additive synthesis unit with an acid catalyst.

Aspect 2: The method of Aspect 1, wherein the feed stream comprises a portion of an effluent from a fluid catalytic cracking process.

Aspect 3: The method of any of the preceding aspects, wherein the feed stream comprises methyl acetylene, propylene, 1,3-butadiene, 1,2-butadiene, isobutylene, cis-2-butene, trans-2-butene, 1-butene, propene, isobutane, n-butane, or a combination thereof.

Aspect 4: The method of any of the preceding aspects, wherein greater than or equal to 95 weight %, preferably greater than or equal to 96 weight %, of the butadiene in the first product stream is transformed into the second product stream.

Aspect 5: The method of any of the preceding aspects, wherein the acid catalyst comprises phosphoric acid, sulfonic acid, sulfuric acid, nitric acid, hypophosphorous acid, metal oxide, zeolite, or a combination thereof.

Aspect 6: The method of Aspect 5, wherein the acid catalyst comprises a sulfonic acid resin, sulfonated polystyrene, hypophosphorous acid, supported niobium oxide, zeolite supported acid catalyst, or a combination thereof.

Aspect 7: The method of any of the preceding aspects, wherein the second product stream is converted into the fuel additive at a temperature of 25° C. to 300° C., preferably 30° C. to 250° C., more preferably 140° C. to 200° C.

Aspect 8: The method of any of the preceding aspects, wherein the second product stream is converted into a fuel additive at a pressure of 0.25 MegaPascal to 20 MegaPascal, preferably 0.5 MegaPascals to 10 MegaPascals, more preferably 5 MegaPascal to 10 MegaPascal.

Aspect 9: The method of any of the preceding aspects, further comprising passing a water stream through the fuel additive synthesis unit.

Aspect 10: The method of Aspect 9, wherein a molar ratio of water to butene fed to the fuel additive synthesis unit is 0.5 to 25, preferably 1 to 20.

Aspect 11: The method of any of the preceding aspects, further comprising withdrawing a by-product stream from the fuel additive synthesis unit and passing the by-product stream through a second hydrogenation unit.

Aspect 12: The method of Aspect 11, wherein the by-product stream comprises 1-butene, 2-butene, isobutane, n-butane, or a combination thereof.

Aspect 13: The method of Aspect 11 or Aspect 12, further comprising withdrawing a recycle stream from the second hydrogenation unit, wherein the recycle stream comprises n-butane, isobutane, or a combination thereof, and recycling the recycle stream back to the feed stream.

Aspect 14: The method of Aspect 13, further comprising passing the recycle stream through the steam cracker to produce propylene, ethylene, or a combination thereof.

Aspect 15: The method of any of the preceding aspects, wherein the first hydrogenation unit and/or the second hydrogenation unit comprises an oscillating baffle reactor, a fixed bed reactor, a fluidized bed reactor, a membrane integrated reactor, or a combination thereof.

Aspect 16: The method of any of the preceding aspects, wherein the fuel additive synthesis unit comprises an oscillating baffle reactor, a fixed bed reactor, multitubular reactor, a membrane integrated reactor, a reactive distillation unit, or a combination thereof.

Aspect 17: The method of any of the preceding aspects, further comprising withdrawing a fuel additive from the fuel additive synthesis unit, wherein the fuel additive comprises 2-butanol, tert-butyl alcohol, C4 dimer, or a combination thereof, preferably wherein the C4 dimer comprises di-isobutylene, 2,2,4-trimethylpentane, 2,3,3-trimethylpentante, or a combination thereof.

Aspect 18: The method of any of the preceding aspects, wherein the fuel additive comprises trimethylpentane in an amount greater than or equal to 0.01 weight %, preferably greater than or equal to 0.02 weight %, more preferably greater than or equal to 0.1 weight %, based on the total weight of the fuel additive.

Aspect 19: The method of any of the preceding aspects, wherein a Research Octane Number of the fuel additive is greater than or equal to 85, preferably greater than or equal to 86.

Aspect 20: The method of any of the preceding aspects, wherein a Reid vapor pressure of the fuel additive is less than or equal to 55 Kilopascals, preferably 8 Kilopascals to 53 Kilopascals, more preferably 10 Kilopascals to 51 Kilopascals.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like. In a list of alternatively useable species, "a combination thereof" means that the combination can include a combination of at least one element of the list with one or more like elements not named. Also, "at least one of" means that the list is inclusive of each element individually, as well as combinations of two or more elements of the list, and combinations of at least one element of the list with like elements not named.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
producing a first product stream comprising butadiene by passing a feed stream comprising C4 hydrocarbons through a steam cracker;
transforming greater than or equal to 90 weight % of the butadiene in the first product stream into a second product stream by passing the first product stream through a first hydrogenation unit comprising three hydrogenation reactors in series, including wherein carbon monoxide is injected into the third reactor wherein the second product stream comprises 1-butene, 2-butene, n-butane, isobutylene, isobutane, or a combination thereof and less than or equal to 1% by weight butadiene; and
converting the second product stream into the fuel additive by passing the second product stream through a fuel additive synthesis unit with an acid catalyst.

2. The method of claim 1, wherein the feed stream comprises a portion of an effluent from a fluid catalytic cracking process.

3. The method of claim 1, wherein the feed stream comprises at least one of methyl acetylene, propylene, 1,3-butadiene, 1,2-butadiene, isobutylene, cis-2-butene, trans-2-butene, 1-butene, propene, isobutane, or n-butane.

4. The method of claim 1, wherein greater than or equal to 95 weight % of the butadiene in the first product stream is transformed into the second product stream and the second product stream comprises less than or equal to 10 weight % isobutylene based on total weight of the second product stream.

5. The method of claim 1, wherein the acid catalyst comprises at least one of phosphoric acid, sulfonic acid, sulfuric acid, nitric acid, hypophosphorous acid, a metal oxide, or a zeolite.

6. The method of claim 1, wherein the acid catalyst comprises at least one of a sulfonic acid resin, sulfonated polystyrene, hypophosphorous acid, a supported niobium oxide, or a zeolite supported acid catalyst.

7. The method of claim 1, wherein the second product stream is converted into the fuel additive at a temperature of 25° C. to 300° C.

8. The method of claim 1, wherein the second product stream is converted into a fuel additive at a pressure of 0.25 MegaPascal to 20 MegaPascal.

9. The method of claim 1, further comprising passing a water stream through the fuel additive synthesis unit.

10. The method of claim 9, wherein a molar ratio of water to butene fed to the fuel additive synthesis unit is 0.5 to 25.

11. The method of claim 1, further comprising withdrawing a by-product stream from the fuel additive synthesis unit and passing the by-product stream through a second hydrogenation unit.

12. The method of claim 11, wherein the by-product stream comprises at least one of 1-butene, 2-butene, isobutane, or n-butane.

13. The method of claim 11, further comprising withdrawing a recycle stream from the second hydrogenation unit, wherein the recycle stream comprises n-butane or isobutane or a combination thereof, and recycling the recycle stream back to the feed stream.

14. The method of claim 13, further comprising passing the recycle stream through the steam cracker to produce propylene or ethylene or a combination thereof.

15. The method of claim 1, wherein the first hydrogenation unit and/or the second hydrogenation unit comprises at least one of an oscillating baffle reactor, a fixed bed reactor, a fluidized bed reactor, or a membrane integrated reactor.

16. The method of claim 1, wherein the fuel additive synthesis unit comprises at least one of an oscillating baffle reactor, a fixed bed reactor, multitubular reactor, a membrane integrated reactor, or a reactive distillation unit.

17. The method of claim 1, further comprising withdrawing a fuel additive from the fuel additive synthesis unit, wherein the fuel additive comprises at least one of 2-butanol, tert-butyl alcohol, or a C4 dimer.

18. The method of claim 1, wherein the fuel additive comprises trimethylpentane in an amount greater than or equal to 0.01 weight %, based on the total weight of the fuel additive.

19. The method of claim 1, wherein a Research Octane Number of the fuel additive is greater than or equal to 85.

20. The method of claim 1, wherein a Reid vapor pressure of the fuel additive is less than or equal to 55 Kilopascals.

* * * * *